United States Patent [19]

Miller et al.

[11] Patent Number: 4,918,585
[45] Date of Patent: Apr. 17, 1990

[54] MAINTENANCE REMINDER SYSTEM FOR A PUMP

[75] Inventors: Les A. Miller, San Jose; Vance J. Nau, Cupertino; Ronald E. Honganen, Campbell; Chih-Hua Chung, Fremont, all of Calif.

[73] Assignee: Spectra Physics, Inc., San Jose, Calif.

[21] Appl. No.: 142,371

[22] Filed: Jan. 11, 1988

[51] Int. Cl.$^4$ .............................................. F04B 49/00
[52] U.S. Cl. .................................. 364/185; 364/509; 210/97; 210/143
[58] Field of Search ............... 364/185, 500, 502, 509, 364/510, 497; 210/656, 662, 97, 143; 417/18; 73/23.1, 61.1 C; 422/70

[56] References Cited

U.S. PATENT DOCUMENTS

| | | | |
|---|---|---|---|
| 3,896,827 | 7/1975 | Robinson | 134/56 D |
| 4,128,476 | 12/1978 | Rock | 210/101 |
| 4,137,011 | 1/1979 | Rock | 417/22 |
| 4,512,442 | 4/1985 | Moore et al. | 187/133 |
| 4,552,513 | 11/1985 | Miller et al. | 417/18 |
| 4,752,283 | 6/1988 | Copeland et al. | 134/109 |

OTHER PUBLICATIONS

Spectra Physics SP8700 Solvent Delivery System, 12 pages, published for Spectra-Physics.

Primary Examiner—Allen MacDonald
Attorney, Agent, or Firm—Skjerven, Morrill, MacPherson, Franklin & Friel

[57] ABSTRACT

There is disclosed a maintenance reminder system for a pump. The system of the invention is coupled to the pump or the control system for the pump and determines the volume of fluid pumped by the pump. In the preferred embodiment, a piston pump is used and piston strokes are counted and converted to total volume of liquid pumped. The computer of the system maintains a database for each maintenance item containing the threshold value for each item and the total volume pumped since the last maintenance. When the total volume exceeds the threshold, a maintenance reminder is displayed and the user may display information from the database as to which item needs service. The computer updates the appropriate fields of the database after the service is performed.

23 Claims, 3 Drawing Sheets

MAINTENANCE REMINDER SYSTEM FOR A PUMP

BACKGROUND OF THE INVENTION

The invention pertains to the field of liquid chromatography (hereafter LC), and, more particularly, to the field of maintenance reminder systems for the pumps of LC systems.

Pumps for LC systems must provide very reliable pumping action to allow the control system for the pump to control it in such a manner as to provide a constant flow rate of solvent through the pump. Typically, such pumps involve seals which have a limited life, pistons which may become scratched and check valves which may become leaky. Since a constant flow rate is very important to LC systems and since the pressures involved are typically very high, the slightest defect in the pump can seriously impair the effectiveness of the system. Currently, the applicants are not aware of any systems on the market which can provide LC system users with reminders of when a maintenance inspection of invidual components of a pump should be performed.

SUMMARY OF THE INVENTION

According to the teachings of the invention, there is provided a maintenance reminder system for a pump. In the preferred embodiment, the invention is coupled to the control system of the pump. The control system provides to the apparatus of the invention a signal from which can be derived information as to when each stroke of one or more pistons in the pump has occurred. Typically, the control system is coupled to the shaft of the pump and to the pump motor drive system. An index signal is generated upon completion of each revolution of the pump shaft. The maintenance reminder system counts piston strokes and converts this information into liters of fluid pumped from the known displacement of each piston. In the preferred embodiment, the user may supply a threshold in terms of liters pumped for each specific element of the pump for which maintenance should be periodically performed. In other emodiments, this threshold may be set at a fixed, predetermined amount for each individual element or a single threshold can be used. The maintenance reminder system updates non volatile RAM each time another liter is pumped, and compares the liters pumped to the threshold for each element. When the actual liters pumped since the last maintenance on any particular item equals or exceeds the threshold set for that item, a maintenance needed reminder is displayed. The user can, in the preferred embodiment, have more detail displayed or printed as to the status of all the items, and this display will have an indication of which items are over their threshold.

DETAILED DESCRIPTION OF THE PREFERRED EMBODIMENT

Figure 1:
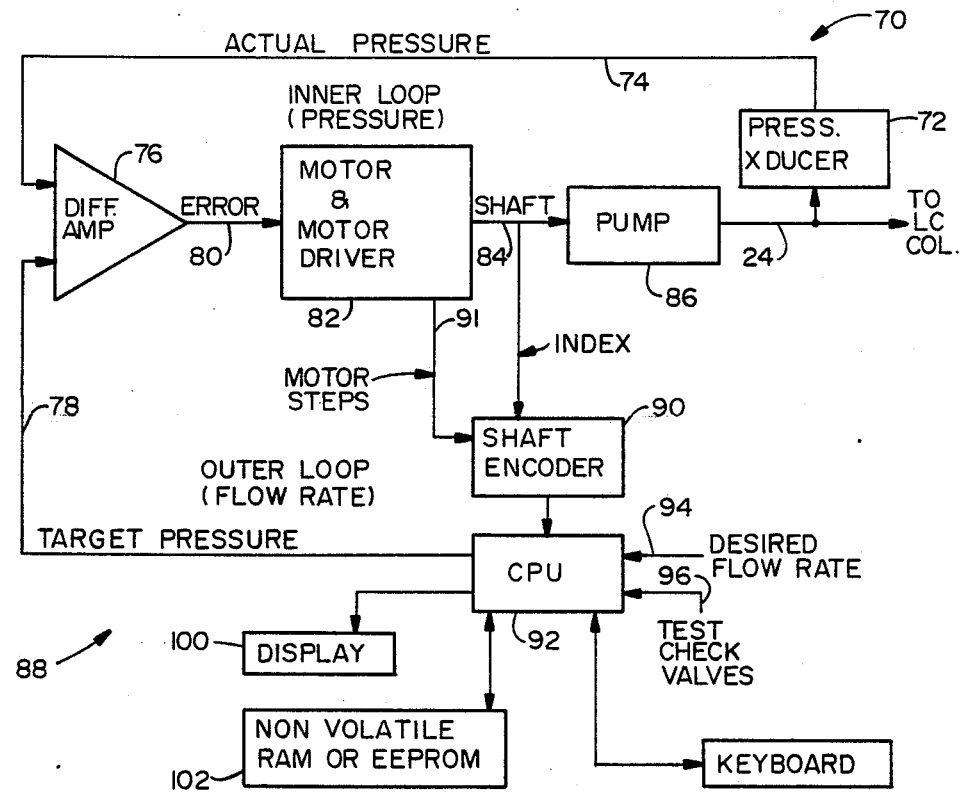
FIG. 1 is block diagram of a typical pump control system in which the maintenance reminder system of the invention can reside.

Referring to FIG. 1, there is shown a block diagram of a typical pump control system in which the system of the invention can find use. An inner loop 70 senses the actual pressure on the outlet line 24 to the column via a pressure transducer 72 and uses the actual pressure signal from the transducer on line 74 as one input to a differential amplifier 76. The other input to this amplifier is the target pressure signal on line 78 from an outer loop 88. These two signals are compared to generate an error signal on line 80. The error signal is coupled to the motor driver and motor 82 and controls the motor speed. The motor drives a shaft 84 which drives the pump 86. The outer loop 88 senses the shaft speed via a shaft encoder or other device 90. The shaft encoder generates a signal used by a computer 92 to determine the pump speed and to determine the flow rate of solvent in the output line 24. The computer also receives a desired flow rate signal on line 94 and uses this signal to compare to the actual flow rate as indicated by the signal from the shaft encoder to set a target pressure signal on line 78 to correct the actual flow rate toward the desired flow rate. The shaft encoder also provides data regarding the absolute shaft position relative to an index point. This data provides the computer with real time information as to the actual position of each of the cams in the pump 86 and the status of the pistons of the pump at each point in time. An index point is in the rotation of the shaft 84 defined which defines a known position of the cams and the pistons. The pump is driven by a stepper motor 82. The steps of the stopper motor 82 translate to known translations of the shaft 84. The computer is coupled to the motor driver through the line 91 so that the steps can be counted and the shaft position at any point in time may be known. The computer 92 is also coupled to a display 100 and to non volatile RAM 102, which, in the preferred embodiment, is EEPROM.

The maintenance reminder system of the invention is implemented by a program run by the computer 92. The computer 92 also runs a pump control program to generate the target pressure signal from the computed shaft speed of the pump and the desired flow rate supplied on line 94. Part of this pump control program is a housekeeping routine which takes care of miscellaneous functions most of which are irrelevant to the teachings of the invention. Part of the function of the maintenance reminder system is to check a maintenance due flag which is set by the main program of the maintenance reminder system when some element of the pump has reached or exceeded its maintenance threshold. Typically, the maintenance reminder system is a subroutine of the housekeeping routine, but it may be a stand alone program in other embodiments.

The first step in the program to perform the maintenance reminder task is to get the stroke count as symbolized by step 120. This step symbolizes any routine to count the strokes. In some embodiments, there may be a counter in the main pump control program (not shown) which increments each time an index signal occurs indicating another revolution has been completed. In other embodiments, the step 120 may symbolize an interrupt service routine which is performed each time the index signal occurs and which increments a counter. There are many different ways of determining when another stroke has been completed, and the particular manner chosen is not critical to the invention.

The next step 122 represents a test as to whether another stroke has been completed. It may be eliminated in embodiments wherein the step 120 is not reached until it is known that another stroke has been completed such as embodiments which service an interrupt generated upon the occurrence of the index signal. For embodiments where the stroke count is kept in a separate counter and where step 120 represents the process of getting the count from that counter, the test 122 represents the process of comparing the old count and the new count to determine if another stroke has been completed. If not, control is returned to the housekeeping routine which then goes about its other business. If another stroke has been completed, step 124 is performed.

Figure 2A:
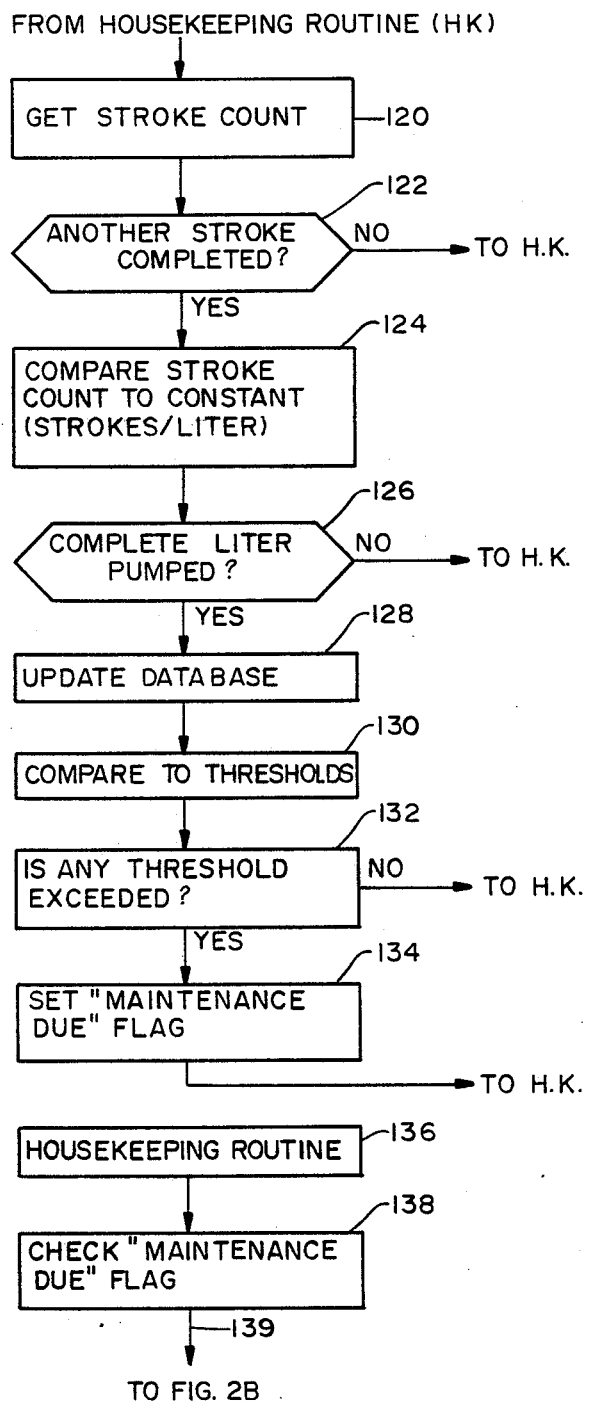
FIGS. 2A and 2B are a flow chart of the program that implements the maintenance reminder system.
Figure 2B:
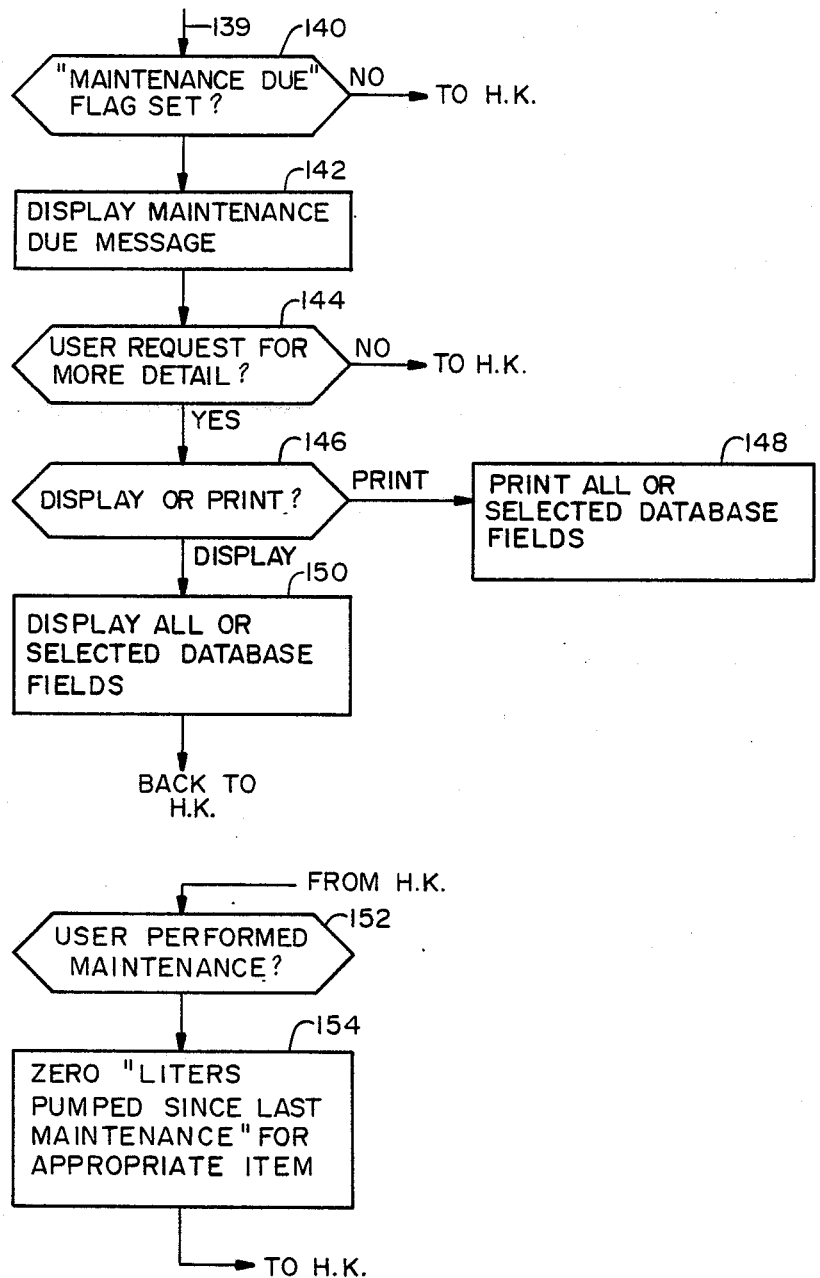

Step 124 represents the process of comparing the stroke count (if the embodiment of FIG. 2 represents an interrupt service routine, a stroke counter will be incremented as part of step 124) to a constant equal to the number of strokes per liter. Next, step 126 is performed. The purpose of this step is to determine whether a complete liter has been pumped because the non volatile RAM is updated only after a complete liter has been pumped. In alternative embodiments, the memory may be updated on every stroke or after a predetermined number of strokes. Step 126 symbolizes whatever comparison is necessary to determine whether a complete liter has been pumped since the last update of the database.

If a complete liter has been pumped, step 128 updates the data base. Each item which need periodic maintenance in the pump has a database record which contains at least two fields and preferably four fields. In a minimum configuration embodiment, the database record for each maintenance item contains a field for the threshold in terms of the whole number of liters that may be pumped between maintenance operations for that item. In the preferred embodiment, this field is user accessible and may be changed by the user. Another field stores the actual number of liters that have been pumped since the last maintenance on that item. It is this field which is updated by incrementation in step 128. In the preferred embodiment, the database also has a third field which used in the case of power failures and which stores the fractional number of liters which have been pumped since the last update. Although the steps to do this update upon a power failure are not shown in the flow chart of FIG. 2, it should be understood that the teachings of the invention contemplate such a function in some embodiments. A fourth field of the data base is the date the last maintenance was performed.

Next, a step 130 is performed to compare the actual liters pumped since the last maintenance for each item to the threshold for that item. Step 132 represents a check to determine if any item's threshold has been exceeded. If not, control is returned to the housekeeping routine. If a threshold has been exceeded, step 134 sets a maintenance due flag. Control is then returned to the housekeeping routine.

The housekeeping routine symbolized by clock 136 checks the maintenance due flag upon the occurrence of either of two events in the preferred embodiment. These events are pump initialization upon start up for a new run and upon the passage of approximately 10 hours from the last check of the maintenance due flag. In other embodiments, the maintenance due flag may be checked periodically or upon the occurrence of different or more events. These checks are symbolized by block 138. Processing then proceeds to step 140 via line 139.

Step 140 is a test to determine if the maintenance due flag is set. If it is not set, control is returned to the housekeeping routine. If it is set, step 142 is performed to display a maintenance due message.

In some embodiments, the next step would be to automatically display the details of the database for all the maintenance items and highlight the items needing maintenance or to display the database fields for those items needing maintenance. In the preferred embodiment, step 144 if performed to determine is the user is requesting more detail. In some embodiments, this may be done by a display prompt asking the user if more detail is requested and monitoring a keyboard or some switch for a predetermined response. In other embodiments, step 144 may represent an interrupt vector generated when the user requests more detail.

When more detail is to be provided, step 146 is performed to prompt the user to determine if the data is to be displayed or printed. If the user selects the print option, all the database records or the records for selected items are printed as symbolized by step 148. If the display option is selected, all the database records or selected ones of them are displayed as symbolized by block 150. Control is then returned to the housekeeping routine.

Step 152 represents the step of monitoring when the user performs the required maintenance. In the preferred embodiment, when the user performs the maintenance, the user accesses the data base and enters the date of performing the maintenance in the appropriate field of the database record for the item serviced. Step 152 represents the process of enabling the user to enter the database and make this entry or, in alternative embodiments, symbolizes the process of prompting the user for the identification of the item serviced and the data of the service. Step 154 is then performed to zero the "liters pumped since last maintenance" field of the appropriate item in the preferred embodiment. In alternate "prompting" embodiments, step 154 also represents the step of updating the "date of last maintenance" field.

Although the invention has been described in terms of the preferred and various alternative embodiments disclosed herein, those skilled in the art will appreciate other alternative embodiments which do not depart from the true spirit and scope of the invention. For example, the system of the invention could be adapted to a turbine type pump with modifications to allow the pump maintenance system to detect the flow rate from the pump and the elapsed time at each flow rate. Further such flow rate and elapsed time data could also be used in piston pump applications as described above by using the computed shaft speed and elapsed time computed by the main pump control program instead of the index signal. All such embodiments are intended to be included within the scope of the claims appended hereto.

What is claimed is

1. An apparatus for providing maintenance reminders for a pump comprising:

control means for said pump which generates at least one signal from which can be derived information indicating when another pump stroke has been completed;

calculating means coupled to said signal for calculating the volume of liquid which has been pumped since the last maintenance and for comparing said volume to a threshold value and for displaying a maintenance reminder if the threshold is exceeded.

2. The apparatus of claim 1 wherein said calculating means counts pump strokes of a pump piston and converts the number of strokes to volume of fluid pumped.

3. The apparatus of claim 1 further comprising memory means coupled to said calculating means for storing the results calculated by said calculating means and said threshold value and further comprising means coupled to said memory means for providing access to said threshold value such that said threshold value may be changed.

4. The apparatus of claim 3 wherein a separate threshold value is stored in said memory means for each of a plurality of items in said pump that require periodic maintenance, and wherein said calculation means includes means to compare the actual volume of fluid pumped since the last maintenance to the threshold for each said item.

5. The apparatus of claim 4 further comprising means coupled to said memory means for maintaining data records in said memory means storing said threshold value for each said item, the actual volume of fluid pumped by said pump since the last maintenance on each said item and the date of the last maintenance for each said item and for updating said data records to zero the actual volume pumped since the last maintenance for a particular item when that item is serviced and for updating in the appropriate data record or records the data of last maintenance for a particular item with the date when said maintenance was performed.

6. The apparatus of claim 5 wherein said calculating means includes means for displaying the data in said data records upon receiving a request to do so.

7. The apparatus of claim 1 wherein said pump includes a plurality of components which need periodic maintenance and further comprising means in said calculating means for maintaining a separate threshold for each said component where said threshold is expressed as the number of volume units that may be pumped between maintenacne service on that component and for maintaining the actual number of volume units that have been pumped since the last maintenance, and wherein said calculating means includes means for determining when each new pump stroke has been completed and for calculating the volume of liquid that has been pumped during each stroke and for updating the record of actual volume units pumped for each component since the last maintenance upon completion of each pump stroke.

8. The apparatus of claim 7 further comprising means in said calculating means for providing programmability to the threshold for each said component.

9. The apparatus of claim 8 further comprising means in said calculating means for storing the fractional number of volume units that have been pumped for each said component since the last update of the data record storing the number of actual volume units pumped since the last maintenance on each said component.

10. The apparatus of claim 9 further comprising means in said calculating means to store a record of the date when the last maintenance was performed for each said component.

11. The apparatus of claim 10 further comprising means in said calculating means for comparing the record of actual volume units pumped since the last maintenance for each component against the corresponding threshold for said component and for setting a maintenance due flag when any threshold has been exceeded.

12. The apparatus of claim 11 further comprising means for checking for a set maintenance due flag upon pump startup and upon passage of a predetermined interval from the last check of said maintenance due flag.

13. An apparatus for providing maintenance reminders for a pump having a plurality of components each of which needs periodic maintenance at various intervals comprising:
control means for said pump which generates at least one signal from which can be derived information indicating when another pump stroke has been completed;
first means coupled to said signal for determining when another pump stroke has been completed and for calculating the volume pumped by the completed stroke;
second means coupled to said first means for maintaining data records for each component of said pump including the maintenance threshold expressed as the volume of liquid that may be pumped between maintenance events and the actual volume of liquid pumped since the last maintenance and further comprising means to update said data record of the actual volume of liquid pumped since the last maintenance upon the completion of each stroke;
third means coupled to said second means for comparing the actual volume of liquid pumped since the last maintenance to the threshold for each component and setting a maintenance due flag when any threshold is exceeded;
fourth means for checking said maintenance due flag upon the occurrence of predetermined events.

14. The apparatus of claim 13 wherein said fourth means includes means for checking said maintenance due flag upon pump startup and at predetermined intervals thereafter.

15. The apparatus of claim 14 further comprising fifth means for displaying the data records upon receipt of a request to do so.

16. The apparatus of claim 15 wherein said second means includes means for providing programmability to said thresholds and means for resetting the actual volume pumped since the last maintenance data record to 0 upon completion of maintenance on the corresponding pump component.

17. A method for keeping track of maintenance needs for a pump having a component which need periodic maintenance comprising the steps of:
sensing the completion of each pump stroke;
calculating the volume of liquid pumped on the stroke just completed;
updating a data record of the total volume of liquid pumped since the last maintenance of said component by adding the liquid pumped during the just completed stroke to said total volume;
comparing the total volume of liquid pumped since the last maintenance to a maintenance threshold expressed as the total preferred volume that may be pumped before performing periodic maintenance on said component;
setting a maintenance due flag if said threshold has been exceeded.

18. The method of claim 17 wherein said updating step includes the steps of updating a plurality of data records each storing the total volume pumped since the last maintenance on one of a plurality of components needing periodic maintenance at periodic intervals, and wherein said step of comparing includes the steps of comparing the actual volumes pumped since last maintenance for each of said plurality of components to the corresponding maintenance threshold for that component and wherein the step of setting the maintenance due flag includes the step of setting the maintenance due flag if any maintenance threshold has been exceeded.

19. The method of claim 18 further comprising the steps of checking for a set maintenance due flag upon pump startup and every 10 hours thereafter.

20. The method of claim 19 further comprising the steps of displaying the data records of actual volumes pumped and the maintenance due thresholds for each said component upon request.

21. The method of claim 20 further comprising the step of providing an opportunity to a user to alter the maintenance due threshold data records to a different volume or volumes for any or all of said components.

22. The method of claim 21 further comprising the step of providing the opportunity to set to 0 the data record for actual volume pumped since the last maintenance service for each component after maintenance on that component has been completed.

23. An apparatus for providing maintenance reminders for a pump comprising:
control means for said pump which generates at least one signal from which can be derived information indicating pump wear;
calculating means coupled to receive said signal for calculating from said signal a wear number having a value indicative of possible pump wear since the last maintenance and for comparing said wear number to a threshold value and for displaying a maintenance reminder if the threshold is exceeded.

* * * * *